United States Patent [19]

Bays et al.

[11] 4,028,404

[45] June 7, 1977

[54] ACETIC ACID DERIVATIVES

[75] Inventors: David Edmund Bays; Roy Vivian Foster, both of London, England

[73] Assignee: Allen & Hanburys Limited, England

[22] Filed: Apr. 26, 1974

[21] Appl. No.: 464,381

Related U.S. Application Data

[60] Continuation-in-part of Ser. No. 372,511, June 22, 1973, abandoned, which is a division of Ser. No. 747,435, July 27, 1968, Pat. No. 3,828,093.

[30] Foreign Application Priority Data

Feb. 22, 1974   United Kingdom ............... 8218/74
July 31, 1967   United Kingdom ............. 35166/67

[52] U.S. Cl. .................... 260/515 R; 260/247.1 R; 260/465 R; 260/469; 260/590 C; 260/592; 424/308; 424/317

[51] Int. Cl.² .................... C07C 63/33; C07C 69/95

[58] Field of Search ...................... 260/515 R, 469; 424/308, 317

[56] References Cited

UNITED STATES PATENTS 3,839,431   10/1974   Sheehan et al. ............... 260/515 R

FOREIGN PATENTS OR APPLICATIONS 1,226,344   3/1971   United Kingdom ............... 260/517

Primary Examiner—Jane S. Myers

[57] ABSTRACT

Novel phenylacetic derivatives are provided of the general formula

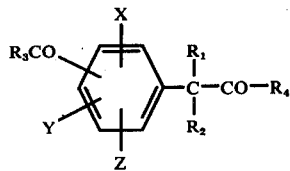

in which $R_1$, $R_2$, $R_3$ and $R_4$ are as defined herein, and pharmaceutically acceptable salts thereof. These have anti-inflammatory or analgetic activity. The invention also provides a process for the production of these compounds from a ketone of the structure:

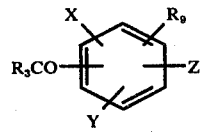

It also provides pharmaceutical compositions including phenylacetic derivatives.

14 Claims, No Drawings

ACETIC ACID DERIVATIVES

This is a continuation-in-part of our copending application Ser. No. 372,511, filed June 22, 1973, now abandoned, which is in turn a divisional of our copending application Ser. No. 747,435, filed July 27, 1968, now U.S. Pat. No. 3,828,093, both of which being hereby incorporated herein by reference thereto.

This invention relates to novel phenylacetic acid derivatives possessing anti-inflammatory, or analgetic activity and to compositions containing the same.

The present invention provides phenylacetic acid derivatives of the general formula (I):

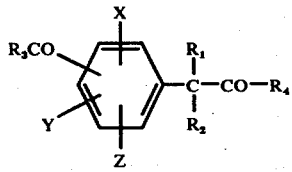

in which the group $R_3CO-$ may only be meta or para oriented with respect to the side chain $-CR_1R_2COR_4$ and in which $R_1$ and $R_2$, which may be the same or different, represent a hydrogen atom or alkyl containing 1 to 6 carbon atoms, $R_3$ represents a cycloalkyl radical containing from 3 to 9 carbon atoms, $R_4$ is a hydroxy or lower alkoxy group containing 1 to 6 carbon atoms, and X, Y and Z are hydrogen.

This invention also provides physiologically acceptable salts of these compounds and optically active forms and racemic mixtures of the compounds which possess asymmetric carbon atoms, i.e. those compounds in which $R_1$ and $R_2$ represent different radicals.

A preferred group of compounds have the general formula:

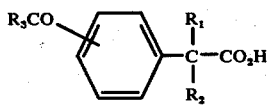

in which $R_3$ represents cyclopropyl, cyclobutyl, cyclopentyl and cyclohexyl, and $R_1$ and $R_2$ represent independently hydrogen or lower alkyl of 1 to 4 carbon atoms and the group $R_3CO$ is in the *m* or *p* position to the side chain $CR_1R_2COOH$, with the proviso that when $R_3$ is cyclopropyl this is in the *m*-position to said side chain, and salts and simple esters thereof.

Particularly preferred compounds according to the invention are:
p-(Cyclobutylcarbonyl)phenylacetic acid
m-(Cyclopropylcarbonyl)phenylacetic acid
p-(Cyclohexylcarbonyl)hydratropic acid We have made the unexpected discovery that certain of the compounds according to the invention possess anti-inflammatory and analgetic activity of great potential utility. Thus, those compounds in which $R_3$ represents cyclopropyl, cyclobutyl and cyclohexyl are particularly active in those tests designed to test anti-inflammatory action.

The compounds may be formulated for use in human and veterinary medicine for therapeutic purposes. The invention therefore also provides pharmaceutical compositions comprising as active ingredients compounds of the general formula (I). Such compositions may be presented for use in a conventional manner with the aid of carriers or excipients and formulatory agents as are required and with or without supplementary medicinal agents. These compositions include, for example, solid and liquid preparations for oral use, suppositories, and injections. It is most convenient to use capsules or tablets which may be prepared according to conventional methods and may be coated if desired for oral administration. Injections may be formulated with the aid of physiologically acceptable carriers and agents as solutions, suspensions or as dry products which are reconstituted before use.

The daily dose of the active ingredient is adjusted to the need of the patient and may for example be from 25 to 500 mgm per day in divided doses depending on the age, weight and condition of the patient.

The compounds of general formula (I) may be prepared from the appropriately substituted ketone of general formula (II)

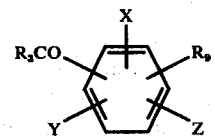

where $R_3$, X, Y and Z have the meanings given above and $R_9$ may be a halomethyl, acetyl or carboxyl group. These compounds may be prepared by standard routes, for example.

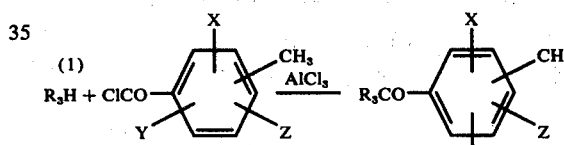

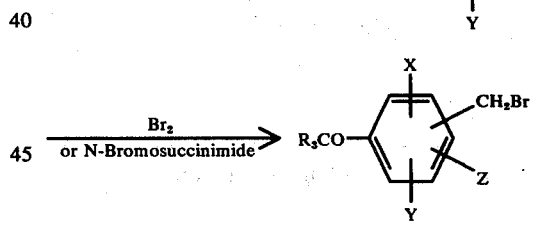

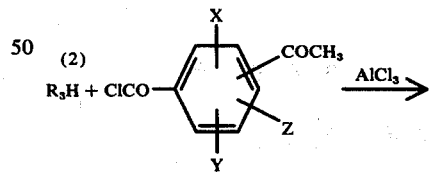

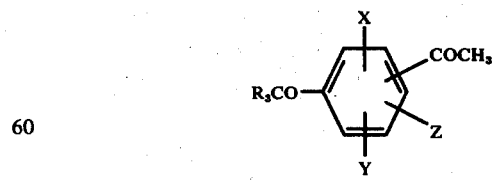

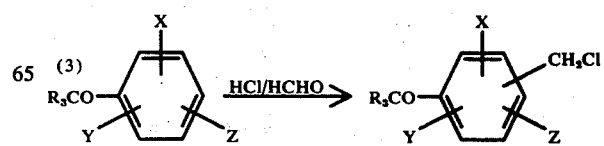

-continued

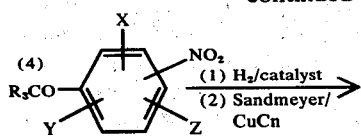

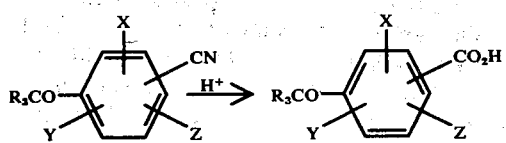

This ketone (II) in which $R_9$ is a bromomethyl group is then reacted further,

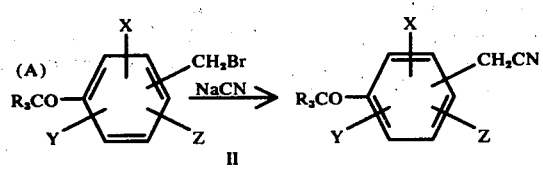

This nitrile may then be reacted further to give compounds according to the invention. For example, hydrolysis with a mixture of acetic acid, water, and sulphuric acid gives the acid (I, $R_4$=OH). Treatment with lower alcohols in the presence of acid catalysts gives the esters (I, $R_4$ = OAlk)

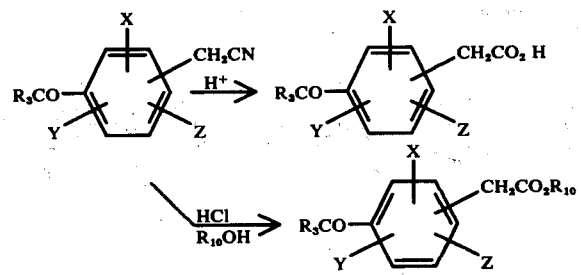

where $R_{10}$ is lower alkyl.

The ketone (II) where $R_9$ is an acetyl group may be reacted according to the Willgerodt reaction.

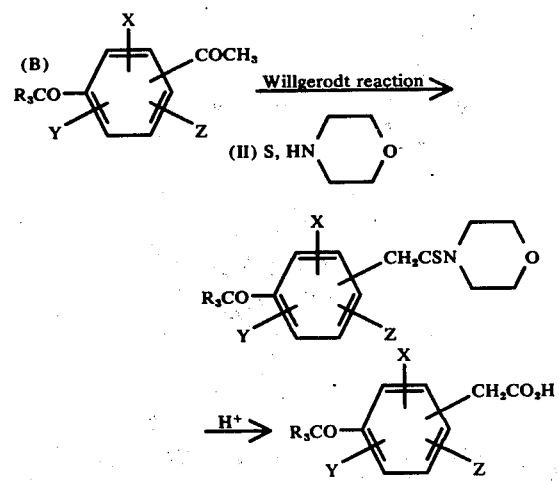

The ketone (II) where $R_9$ is a carboxyl group may be reacted as follows:

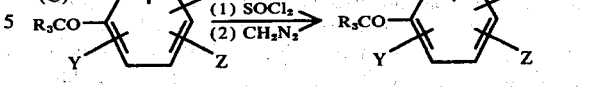

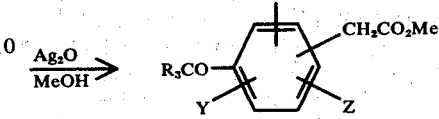

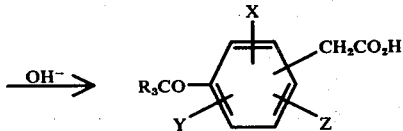

The compounds of general formula (I) in which $R_4$ is alkoxy may also be prepared from the compounds in which $R_4$ is a hydroxy group by conventional methods of esterification, for example by reaction with an alcohol in the presence of an acid catalyst. This product may then be reacted further by conventional methods of transesterification, for example by reaction with an alcohol in the presence of a basic catalyst to give higher or substituted esters.

Compounds of general formula (I) in which $R_1$ and $R_2$ are alkyl may be made by reacting the compounds of formula (I) in which $R_4$ is alkoxy with a suitable base, for example sodium hydride, and reacting the mono- or di-anion so formed with a suitable alkylating agent, for example with methyl iodide.

Salts of the compounds of general formula (I), for example when $R_4$ is a hydroxy group, may also be made by conventional methods, for example by reaction with organic or inorganic bases in a suitable solvent.

For those compounds in which both $R_1$ and $R_2$ represent hydrogen then hydrolysis of the corresponding nitrile, for example with potassium hydroxide and ethyl alcohol is appropriate, as follows:

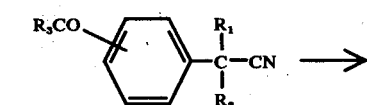

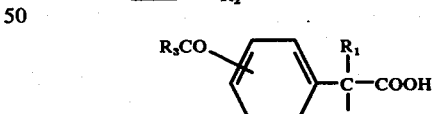

For those compounds of the invention in which $R_1$ is alkyl and $R_2$ is hydrogen, the parent nitrile, prepared by procedures described above is converted into its sodio derivative, which is treated with diethyl carbonate to give the sodio derivative of the corresponding cyanoacetic ester. Treatment of the last with an alkylating agent, for example methyl iodide, gives the alkylated cyanoacetic ester, which on hydrolysis with a mixture of acetic acid and concentrated sulphuric acid affords the compounds of the invention. This reaction is shown in Scheme 1.

Scheme 1

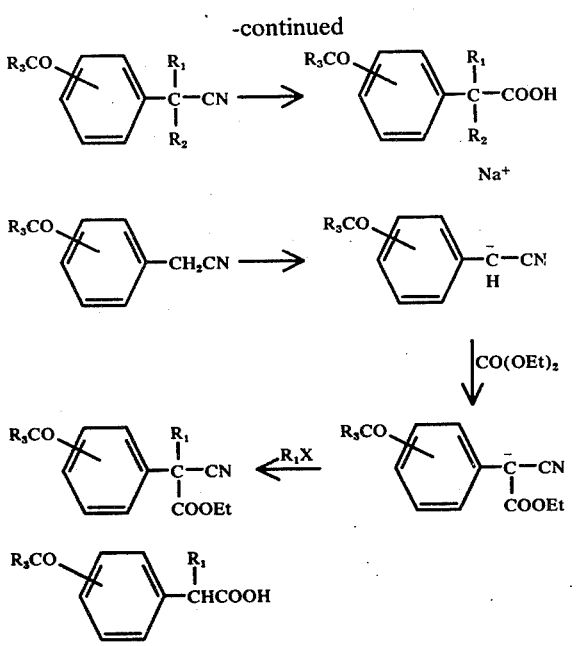

The following Examples illustrate the invention:

EXAMPLE 1

(4-cyclohexylcarbonylphenyl) acetic acid

α-Bromo-p-tolylcyclohexyl ketone

Cyclohexyl p-tolyl ketone (10g.), N-bromosuccinimide (8.8g.) and benzoyl peroxide (0.5g.) in carbon tetrachloride (200 ml.) were heated under reflux for 6.5 hours. Succinimide was filtered off and the solvent evaporated to give an oil (17g.) which contained 70% of the required ketone.

4-cyclohexylcarbonylphenylacetonitrile

Crude α-bromo-p-tolylcyclohexyl ketone (17g.), sodium cyanide (3g.), dioxan (80 ml.) and water (20ml.) were heated under reflux for 4 hours. The mixture when cold was poured into water and extracted with ether. Evaporation of the extracts followed by chromatography on silica gave a solid (1.5g.) which was crystallised from light petroleum (b.p. 60°–80°) m.p. 102°–103°.

(4-cyclohexylcarbonylphenyl) acetic acid 4-cyclohexylcarbonylphenylacetonitrile (1.5g.), water (1.5 ml.), concentrated sulphuric acid (1.5 ml.) and acetic acid (1.5 ml.) were heated under reflux for 6 hours, cooled, poured into water and extracted with ether. Removal of the solvent and crystallisation from cyclohexane gave the acid, m.p. 94°–95.5°.

EXAMPLE 2 p-(Cyclobutylcarbonyl)phenylacetic acid

Cyclobutyl p-tolyl ketone

Cyclobutylcarbonyl chloride (23.8 g.) in dry toluene (25 ml) was added dropwise during 1 hour to a stirred suspension of anhydrous aluminium chloride (29.4 g) in dry toluene (150 ml). After stirring a further 20 minutes, the mixture was poured into iced water (1 l) and the organic layer was separated, washed with water, dried over magnesium sulphate, filtered and evaporated. The residue was distilled under reduced pressure and the fraction b.p. 79–80°/0.03 mm was collected. On standing the product solidified and the solid had m.p. 32°–34°.

α-Bromo-p-tolyl cyclobutyl ketone

Cyclobutyl p-tolyl ketone (30 g) and N-bromosuccinimide (31 g) in carbon tetrachloride (200 ml) were irradiated and heated under reflux with a tungsten lamp for 1.5 hours, and cooled. The mixture was filtered and the filtrate was evaporated. The residue was distilled under reduced pressure and the fraction b.p. 120°–125°/0.015 mm was collected.

p-(Cyclobutylcarbonyl)phenylacetonitrile

α-Bromo-p-tolyl cyclobutyl ketone (18.5 g) in dimethylformamide (50 ml) was added during 35 minutes to sodium cyanide (4 g) in dimethylformamide (100 ml) which was cooled below 10° and stirred. The solution was allowed to warm to 20° during 2 hours and poured into water (1 l). The mixture was extracted with ether (3 × 200 ml) and the combined extracts were dried over magnesium sulphate, filtered and evaporated. The residue was extracted with light petroleum (b.p. 60°–80°) (7 × 250 ml) and the extracts were evaporated to leave an oil which partly crystallised on standing.

p-(cyclobutylcarbonyl)phenylacetic acid p-(Cyclobutylcarbonyl)phenylacetonitrile (8.1 g) in ethanol (50 ml) was added to potassium hydroxide (6.8 g) in water (50 ml) and the mixture was heated under reflux for 5 hours and cooled. The solution was diluted with water (100 ml), washed with ether (2 × 100 ml), acidified to pH 1 with hydrochloric acid and extracted with ether (3 × 100 ml). The combined extracts were dried over magnesium sulphate, filtered and evaporated to give a brown oil. This was extracted with a hot mixture of light petroleum (b.p. 60°–80°) and ethyl acetate (9:1) (3 × 200 ml). The solid that crystallised from the extracts on cooling was collected. It had m.p. 91°–92.5°.

EXAMPLE 3 m-(Cyclopropylcarbonyl)phenylacetic acid

Cyclopropyl m-tolyl ketone m-Bromotoluene (34.2 g) in dry ether (120 ml) was added dropwise to magnesium turnings (4.8 g) in dry ether (100 ml). The heat of reaction maintained the mixture to boiling under reflux during the addition and the mixture was heated under reflux for a further hour. The mixture was cooled to 0°, dry cadmium chloride (19.6 g) was added and the temperature allowed to rise to 20° C. After 1 hour, cyclopropanecarbonyl chloride (20.8 g) in dry ether (50 ml) was added dropwise and the mixture was heated under reflux for 4 hours, cooled to 0° and treated with 2 N hydrochloric acid. The ether layer was separated, washed with aqueous sodium bicarbonate (3 × 100 ml., 8%) and with water, dried over magnesium sulphate, filtered and evaporated. The residue was distilled under reduced pressure and the fraction b.p. 86°–90°/0.4 mm was collected.

α-Bromo-m-tolyl cyclopropyl ketone

A stirred suspension of cyclopropyl m-tolyl ketone (16 g) and N-bromosuccinimide (17.8 g) in carbon tetrachloride (100 ml) was irradiated and heated under reflux by means of a tungsten lamp for 2 hours and cooled. The solid was filtered off and the filtrate evaporated. The residual oil was distilled under reduced pressure and the fraction distilling at 115°–130°/0.1 mm was collected.

m-(Cyclopropylcarbonyl)phenylacetonitrile

α-Bromo-m-tolylcyclopropyl ketone (10 g) in dry dimethylformamide (20 ml) was added dropwise during 1 hour to a stirred suspension of sodium cyanide (1.96 g) in dry dimethylformamide (40 ml). The mixture was cooled to 10° during the addition and for a further hour, then left to stand at 20° for a further 2 hours and poured onto ice (140 g). The mixture was extracted with ethyl acetate (3 × 60 ml) and the extracts were combined, washed with water, dried over magnesium sulphate, filtered and evaporated to give a brown oil.

m-(Cyclopropylcarbonyl)phenylacetic acid m-(Cyclopropylcarbonyl)phenylacetonitrile (8.1 g) and potassium hydroxide (3.36 g) in water (50 ml) and ethanol (50 ml) were heated under reflux for 5 hours and cooled. The mixture was washed with chloroform (2 × 50 ml), acidified to pH 1 with 5N hydrochloric acid and extracted with ethyl acetate (2 × 75 ml). The extracts were combined, washed with water, dried over magnesium sulphate, filtered and evaporated. The residue was distilled under reduced pressure and the fraction b.p. 170°/0.1 mm collected. The distilate solidified and the solid melted at 52°.

EXAMPLE 4 p-(Cyclohexylcarbonyl)hydratropic acid 2-(p-Cyclohexylcarbonyl)phenyl-2-cyanopropionic acid, ethyl ester p-(Cyclohexylcarbonyl)phenylacetonitrile (British Pat. No. 1,226,344) (2.5 g) in diethyl carbonate (13.2 g), was heated to 110°–115° and stirred. Alcoholic sodium ethoxide prepared from sodium (0.275 g) and dry ethanol (5.5 ml) was added and ethanol was allowed to distill from the heated mixture. The mixture was heated to 140° and maintained at this temperature for 2 hours and cooled. Dry ether (25 ml) was added and the solid present was collected and dissolved in ethanol (35 ml). Methyl iodide (5.96 g) was added and the mixture was heated under reflux for 1 hour and evaporated. Ethyl acetate and 2N hydrochloric acid (40 ml) was added and the mixture was shaken. The ethyl acetate layer was separated, washed with water, dried over magnesium sulphate, filtered and evaporated to give a brown oil.

p-(Cyclohexylcarbonyl)hydratropic acid 2-(p-Cyclohexylcarbonyl)phenyl-2-cyanopropionic acid, ethyl ester (2.55 g, crude) was added to a mixture of concentrated sulphuric acid (5 ml), water (5 ml) and glacial acetic acid (17 ml) and the mixture was heated under reflux for 22 hours and cooled. Water (35 ml) was added and the mixture was shaken with ether (2 × 50 ml). The ether solution was extracted with 2N sodium hydroxide (3 × 50 ml) and the alkaline extract was acidified to pH2 with 5N hydrochloric acid. The acidic mixture was extracted with ether (2 × 75 ml) and the extracts were dried over magnesium sulphate, filtered and evaporated to yield a brown oil.

p-(Cyclohexylcarbonyl)hydratropic acid, compound with dicyclohexylamine p-(Cyclohexylcarbonyl)hydratropic acid (1.75 g, crude) in ethyl acetate (15 ml) was treated with dicyclohexylamine (1.5 ml) in ethyl acetate (5 ml) and the mixture was evaporated. The residue was extracted with light petroleum (b.p. 60°–80°) (2 × 50 ml) and the extracts were evaporated. The residue was triturated with dry ether and the solid was collected. It had m.p. 150°–151.5°.

EXAMPLE 5

To prepare 10,000 tablets each containing 100 mg. of the compound of Example 1.

Mix together 1,000 g. of powdered compound of Example 1 with 750 g. of Calcium Sulphate dihydrate and sufficient of a 5% solution of low viscosity sodium carboxymethylcellulose to produce a damp cohesive mass. Granulate the damp mass by passing through a 16 mesh sieve. Dry the granules at 45°–50° C. Pass the dried granules through a 20 mesh sieve and mix the sieved granules with 240 g. of maize starch and 10 g. of magnesium stearate.

Compress the lubricated granules on a suitable tablet machine using 10/32 inch diameter normal concave punches to produce tablets each weighing 200 mg.

EXAMPLE 6

To prepare 100,000 sugar coated tablets each containing 100 mg. of the compound of Example 1.

Mix together 10 kg. of powdered compound of Example 1 with 7.5 kg. of Calcium Sulphate dihydrate and sufficient of a 5% solution of low viscosity sodium carboxymethylcellulose to produce a damp cohesive mass. Granulate the damp mass by passing through a 16 mesh sieve. Dry the granules at 45°–50° C. Pass the dried granules through a 20 mesh sieve and mix the sieved granules with 2.4 kg. of maize starch and 100 g. of magnesium stearate.

Compress the lubricated granules on a suitable tablet machine using 10/32 inch diameter deep concave punches.

Place the tablet cores in a coating pan of suitable size. Heat the cores to 45° C. by means of hot air and apply 200 ml. of a syrup containing 12% by weight of Acacia and 66% by weight of sucrose. Allow the tablets to roll until they are evenly coated with the syrup then dry by means of heated air. Repeat this step.

Continue the sugar coating using a syrup containing 60% by weight of sucrose and 15% by weight of calcium phosphate until the tablet cores each weigh 325 mg.

Continue coatingusing a syrup containing 66% by weight of sucrose and a suitable colouring agent until the tablets weight 350 mg. each. Finally polish the tablets using known techniques.

EXAMPLE 7

To prepare 100,000 enteric coated tablets such containing 100 mg. of the compound of Example 1.

Prepare the tablet cores as described in Example 6.

Rotate the tablet cores in a suitable coating pan and apply 200 ml. of a solution containing 10% by weight of polyvinylpyrrolidone 2% by weight of polyethylene glycol 6000 in 66 o.p. industrial alcohol. Dry off the solvents with cold air and repeat the operation. Apply in a similar manner a film of cellulose acetate phthalate sufficient to enable the tablets to confirm to the distintegration test for enteric coated tablets of the British Pharmacopoeia 1963 p. 1158.

The cellulose is applied in solution in suitable mixed solvents such as acetone/alcohol and may contain plasticisers such as castor oil.

When a satisfactory thickness of cellulose acetate phthalate has been applied the sugar coating procedure as outlined in example 6 is followed.

EXAMPLE 8

Capsules

To prepare 10,000 capsules each containing 50 mg.

Mix together 500 g. finely powdered and 500 g. micro-crystalline cellulose. Fill the mixed powders into No. 4 hard gelatin capsules, each capsule containing 100 mg. of the mixture.

Although Examples 5 to 8 relate to the use of the compound of Example 1 as the active ingredient, any of the compounds of formula I may be used.

What is claimed is:

1. A phenylacetic acid derivative of the general formula:

in which the group $R_3CO-$ may only be meta or para oriented with respect to the side chain $-CR_1-R_2-COR_4$ and in which $R_1$ and $R_2$, which may be the same or different, are each hydrogen or alkyl containing from 1 to 6 carbon atoms, $R_3$ is cycloalkyl containing from 3 to 9 carbon atoms, and $R_4$ is hydroxy or lower alkoxy containing from 1 to 6 carbon atoms, or a pharmaceutically acceptable salt of said derivative in which $R_4$ is hydroxy with an organic or inorganic base.

2. The compound of claim 1, which is (4-cyclohexanoylphenyl) acetic acid.

3. The compound of claim 1, wherein $R_3$ is cyclobutyl.

4. The compound of claim 1, wherein $R_3$ is cyclopentyl.

5. The compound of claim 1, wherein $R_3$ is cyclohexyl.

6. The compound of claim 1, which is p-(cyclobutylcarbonyl)phenylacetic acid.

7. The compound of claim 1, which is p-(cyclohexylcarbonyl)hydratropic acid.

8. An anti-inflammatory and analgetic composition containing an anti-inflammatory effective amount or an analgetic effective amount of the compound of claim 1 and a pharmaceutically acceptable carrier or diluent therefor.

9. The composition according to claim 8, in which the compound is (4-cyclohexylcarbonylphenyl)acetic acid.

10. The composition of claim 8, wherein $R_3$ is cyclobutyl.

11. The composition of claim 8, wherein $R_3$ is cyclopentyl.

12. The composition of claim 8, wherein $R_3$ is cyclohexyl.

13. The composition according to claim 8, in which the compound is p-(cyclobutylcarbonyl)phenylacetic acid.

14. The composition according to claim 8, in which the compound is p-(cyclohexylcarbonyl)hydratropic acid.

* * * * *